United States Patent [19]
Humphrey

[11] Patent Number: 5,368,773
[45] Date of Patent: Nov. 29, 1994

[54] PREPARATION OF SALT SOLUTIONS OF PHOSPHONOCARBOXYLIC ACIDS

[75] Inventor: John Humphrey, Maple, Canada

[73] Assignee: Anco Chemicals Inc., Maple, Canada

[21] Appl. No.: 53,756

[22] Filed: Apr. 29, 1993

[30] Foreign Application Priority Data

Apr. 30, 1992 [CA] Canada .................................. 2067668

[51] Int. Cl.$^5$ ............................................ C23F 11/167
[52] U.S. Cl. .................. 252/389.23; 210/699; 422/15; 423/99
[58] Field of Search .................. 210/699, 66; 252/194, 252/389.23; 422/15; 423/99

[56] References Cited

U.S. PATENT DOCUMENTS

| | | | |
|---|---|---|---|
| 3,933,427 | 1/1976 | Bohnsack et al. | 210/699 |
| 4,057,511 | 11/1977 | Bohnsack et al. | 210/699 |
| 4,497,713 | 2/1985 | Geiger | 210/699 |

OTHER PUBLICATIONS

Hawley's Condensed Chemical Dictionary, 11th edition, p. 208, Van Nostrand Reinhold Company.
Experimental Organic Chemistry, 2nd edition, p. 93, McGraw-Hill Book Company.
Morrison & Boyd, 4th edition, pp. 779–780.

*Primary Examiner*—Robert L. Stoll
*Assistant Examiner*—Valerie Fee
*Attorney, Agent, or Firm*—Bereskin & Parr

[57] ABSTRACT

A substantially 100% active aqueous solution of one or more phosphonocarboxylic acids and one or more hydroxides, wherein the solution has a slightly alkaline pH. In an alternate embodiment, a dry, free flowing mixture comprising one or more phosphonocarboxylic acids, calcium chloride fines which, on average, are a dihydrate, and hydroxide is disclosed.

26 Claims, No Drawings

PREPARATION OF SALT SOLUTIONS OF PHOSPHONOCARBOXYLIC ACIDS

FIELD OF THE INVENTION

This invention relates to methods for the preparation of slightly alkaline salt solutions of phosphonocarboxylic acids and, in a preferred embodiment, slightly alkaline salt solutions of hydroxyphosphonocarboxylic acids. The solutions may be either liquid or solid solutions such as a dry, free flowing solid form of phosphonocarboxylic acid salts.

BACKGROUND TO THE INVENTION

Hydroxyphosphonocarboxylic acids have been used as corrosion inhibitors in rust inhibition systems. For example, the use of such inhibitors, either alone or in combination with other inhibitors such as chromates, is discussed in U.S. Pat. Nos. 4,847,017; 4,052,160; 3,933,427; and 4,057,511.

A problem with the use of phosphonocarboxylic acids, including hydroxyphosphonocarboxylic acids, is that they are extremely acidic by nature. Further, these compounds tend to be corrosive and a potential hazard.

In addition, a further problem which has been encountered in preparing phosphonocarboxylic acid solutions is that some of the phosphonocarboxylic acid may be deactivated during the preparation of the solution and accordingly not available for use in the inhibition system.

SUMMARY OF THE INVENTION

In accordance with the instant invention, a process for preparing a substantially active salt solution of one or more phosphonocarboxylic acids comprises preparing a first solution of one or more phosphonocarboxylic acids, preparing a second solution of one or more hydroxides and mixing a sufficient amount of the first solution into the second solution to obtain a mixture of the first and second solutions having a slightly alkaline pH, the first solution being introduced into the second solution at a rate to maintain the local pH of the mixture less than about 12 during the addition.

In accordance with the instant invention, a process for the production of a dry, free flowing phosphonocarboxylic acid mixture comprises the steps of preparing a mixture of a major proportion of partially hydrated calcium chloride fines and a minor amount of one or more hydroxides, preparing a solution of one or more phosphonocarboxylic acids and adding a sufficient amount of this solution to the mixture, with agitation, at a rate to obtain a dry, free flowing product and to maintain the local pH of the mixture less than about 12 during said addition. The salt solutions of the instant invention may be used as corrosion inhibitors in rust inhibition systems. Typically, rust inhibition systems in refrigeration units, such as systems for skating rinks, use chromated brine systems. The salt solutions of phosphonocarboxylic acids prepared according to the instant invention may be used either as a charge in new refrigeration systems, or, alternately, they can be added to existing refrigeration systems. The instant solutions have the advantage of being chemically neutral in existing systems such that, when they are added to an existing system, the solution does not react with the chromates, or the other chemicals which were already in the system. Accordingly, the phosphonocarboxylic acid solutions of the instant invention are very versatile.

The phosphonocarboxylic acids of the instant invention may be used in a variety of applications. For example, the solutions may be used in any application where a thin layer of a corrosion inhibitor is required. Accordingly, the solution may be used in numerous applications. For example, the material could be used in weighting pneumatic tires.

The process of the instant invention provides a new method for producing phosphonocarboxylic acid salts, for the use in corrosion inhibition systems, in which the phosphonocarboxylic acid is substantially 100% active. The solution obtained by the foregoing process results in the production of a salt solution in which all, or essentially all, of the phosphonocarboxylic acid is active and available for corrosion inhibition.

These and other advantages of the instant invention will be more fully and particularly described in association with the following description of a preferred embodiment of the invention.

DESCRIPTION OF THE PREFERRED EMBODIMENT

A liquid phosphonocarboxylic acid salt solution may be prepared from a mixture of one or more hydroxides and one or more phosphonocarboxylic acids.

The phosphonocarboxylic acid may be any of those known in the art. A mixture of one or more phosphonocarboxylic acids may be used. Preferably, the phosphonocarboxylic acid is a hydroxyphosphonocarboxylic acid and, more preferably, the phosphonocarboxylic acid is a mono-phosphonocarboxylic acid. The phosphonocarboxylic acid is present in an aqueous solution. The concentration of phosphonocarboxylic acid in the aqueous solution may be from about 30 to 60 wt % and, preferably, from about 40 to about 60 wt %, and more preferably about 50 wt %.

The hydroxide may be any of those which are compatible with the system into which the inhibitor is to be placed and preferably, potassium hydroxide is used and, most preferably, a combination of potassium and magnesium hydroxide is used. Further, as discussed below, preferably only a pH limiting amount of magnesium hydroxide is utilized.

According to the process of the instant invention, if more than one hydroxide is used, then the hydroxides may be mixed together at room temperature. Subsequently, the phosphonocarboxylic acid is added to the hydroxide solution to produce a slightly alkaline phosphonocarboxylic acid salt solution. The addition of the phosphonocarboxylic acid to the hydroxides tends to cause a localized increase in the pH of the solution, at least at the point of addition. The degree to which such a localized increase may occur, and the level of such a pH increase, depends upon various factors including the speed with which the chemicals are mixed together as well as the concentration of the hydroxide solution.

The rate of addition of the phosphonocarboxylic acid is adjusted so that the pH of the solution is less than about 12. At a pH greater than about 12, the phosphonocarboxylic acid undergoes a chemical change whereby the activity of the carboxylic acid is decreased. In order to ensure that the resultant salt solution is 100% active, it is important to ensure that the pH of the mixture, at any point, does not increase above 12. Accordingly, the salt solution should be continuously mixed during the addition of the phosphonocarboxylic acid. It has been found that the addition of the phosphonocarboxylic acid may take 2.5–4 hours.

The reaction of the phosphonocarboxylic acid and the hydroxide is very exothermic (about 13.7 Kcal/mole). Preferably, the temperature of the mixture is maintained below about 150° F. If the temperature increases above this level, then substantial evaporation of water may occur. If this occurs, then additional water is required. Further, the evaporation can cause an increase in the local concentration of the mixture and this may result in an increase in the local pH above 12. For this reason, it is preferred to keep the temperature below about 150° F. and, preferably below about 140° F.

As discussed above, preferably, the hydroxide is potassium hydroxide. As the potassium hydroxide is added, the rate of addition may be controlled by monitoring the local pH of the solution to ensure that the local pH is kept below about 12. Thus, no substantial deactivation of the carboxylic acid is realized. Further, by monitoring the temperature of the solution, the local pH may be readily monitored. If the temperature commences to increase too rapidly, then magnesium hydroxide may be added in place of the potassium hydroxide. Alternately, a mixture of potassium and magnesium hydroxides may be used. In particular, the use of a small amount of magnesium hydroxide (referred to herein as a pH limiting amount) assists in reducing the formation of localized increases in pH and, accordingly, in producing a salt solution that is effectively 100% active. It has surprisingly been found that this use of magnesium hydroxide is particularly suited to maintain the temperature of the solution below the desired level.

According to one embodiment of this invention, it is preferred that the mixture of hydroxides comprises a substantial amount of potassium hydroxide and a minor amount of magnesium hydroxide. Large amounts of magnesium hydroxide are not required, and it is possible to use a ratio of potassium hydroxide to magnesium hydroxide which is as low as about 25:1. For example, if an aqueous solution containing approximately 50 wt. % of hydroxides is utilized, then, based upon the total weight of the solution comprising hydroxides and phosphonocarboxylic acid, the potassium hydroxide could comprise about 48 wt % of the total composition, and the magnesium hydroxide could comprise only about 2 wt %.

The phosphonocarboxylic acids react with the hydroxides during the production of the slightly alkaline solution. The reaction takes a while to proceed to completion and, in fact may take one to two days to proceed to completion. Since these solutions are used in rust inhibition systems, the solutions are accordingly slightly alkaline. Preferably, the pH of the solution is from 7.7 to about 9.0 and, more preferably, from about 8.0 to about 8.5. However, the slightly alkaline salt solution may be prepared in a concentrated form and subsequently diluted prior to use. A concentrated solution is a solution having a mole active concentration of from about 150,000 to about 450,000, preferably from about 200,000 to about 450,000 and most preferably about 250,000 ppm phosophonocarboxylic acid. The upper limit of the phosphonocarboxylic acid is based upon the solubility of the salt solution. A concentrated solution may contain up to about 25 wt. % phosphonocarboxylic acid. If such is the case, then the pH of the solution, after the reaction proceeds to completion, may be substantially higher than the preferred pH of from 7.7 to about 9.0 and will have to be diluted. Preferably, the pH of the concentrated solution, after the reaction has proceeded to completion, is about 9.5. Due to the rate of reaction, during the preparation of the solution, it is preferred that the initial pH of the solution after the introduction of the carboxylic acid to the hydroxide is from about 6.5 to about 8.5. Accordingly, the amount of phosphonocarboxylic acid which is added is sufficient such that the pH of the resultant solution is in the range from about 6.5 to about 8.5. Preferably, the pH is about 7.5. Preferably, the weight ratio of phosphonocarboxylic acid to hydroxides is about 1:1.

Preferably, the initial pH of the concentrated solution after the mixing of the carboxylic acid and the hydroxides is from about 6.5 to about 8.5 and, after the reaction is proceeded to completion, about 9.5. If, subsequent to the addition of the phosphonocarboxylic acid, the pH of the solution is above or below 9.5, then it is preferred to adjust the pH to achieve this value. Any acid or alkaline known in the art may be utilized to adjust the pH. However, as will be apparent to those skilled in the art, the acid or alkaline material which is utilized should not deleteriously affect the solution or the system in which the solution is used. For this reason, it is preferred that, if the pH is above 9.5, that the pH is decreased by the addition of an additional amount of phosphonocarboxylic acid, such as BELCOR 575 TM (a 50% active phosphonocarboxylic acid solution). However, if the pH is below 9.5, the pH may be raised by the addition of potassium hydroxide, such as a 45% solution of potassium hydroxide.

By way of example, a phosphonocarboxylic acid salt solution may be produced from the following materials:
  48 wt. % of potassium hydroxide (50% commercial grade)
  2 wt. % of magnesium hydroxide (57–58% solids)
  50 wt. % BELCOR 575 (50% active solution)

The resulting product contains about 25 wt. % active phosphonic ingredients. If the pH were to increase above 12 at any time during the preparation of the composition, then a part of the phosphonocarboxylic acid would be deactivated.

As discussed above, the concentrated solution may then be diluted to a predetermined level for use. As is known in the art, the amount of dilution which is required depends upon the system in which the inhibitor is used. A concentrated solution having about 25 wt. % phosphonocarboxylic acid may be diluted with four parts of water to one part of concentrated solution on a weight for weight basis. This dilution results in a decrease in the pH of the diluted solution. Preferably, the solution is diluted to obtain the desired pH. If such a concentrated solution is diluted on a 4:1 basis, then the pH of the diluted solution will be from about 8.0 to about 8.5.

One problem in refrigeration systems is to ensure that there is a sufficient amount of inhibitor to prevent corrosion. To this end, the level of phosphonics is measured in the system. However, the test measures both active and inactive phosphonics. The test is not able to distinguish between the two. Accordingly, if any deactivation occurs, it is not possible to determine the exact level of inhibitor in the system. One advantage of the instant invention is that, since the salt solution is prepared without deactivating a significant amount of the phosphonics, it is possible to precisely know the amount of inhibitor in the system. Accordingly, by using the neutral salt solution of the instant invention, it is possible to know the exact level of inhibitor in the system.

Accordingly, the instant invention discloses a substantially 100% active aqueous solution of the phosphonocarboxylic acid and one or more hydroxides, wherein the solution may have a pH in the range from about 8.0 to about 8.5. Preferably, the hydroxide is potassium hydroxide or a mixture of potassium and magnesium hydroxides. More preferably, the hydroxide comprises a pH limiting amount of magnesium hydroxide and the remainder of the hydroxide is potassium hydroxide.

If a concentrated solution is prepared, then the phosphonocarboxylic acid salt solution may be diluted, if desired, prior to use. A concentrated solution, such as that described above which contains about 25 wt. % phosphonocarboxylic acid salt, will freeze at a higher temperature than a more diluted solution. This freezing will result in part of the salt precipitating out of the solution. Accordingly, unless care is taken to ensure that the solution does not freeze, it will not be possible to determine accurately the amount of inhibitor in a system. Preferably, the solution is diluted to the point at which the solution will freeze at the lowest possible temperature. The solution may be diluted on a 1:1 weight basis with water to obtain a solution containing about 12.5 wt. % of active inhibitor. Alternately, the solution may be diluted on a 4:1 weight basis with water to obtain a solution having a pH of about 8.0 to about 8.5.

According to the instant invention, it is also possible to produce a dry, free flowing phosphonocarboxylic acid salt mixture. This mixture is prepared from a mixture of modified calcium chloride and one or more phosphonocarboxylic acids. The modified calcium chloride acts as a carrier for the carboxylic acid.

The modified calcium chloride comprises a mixture of calcium chloride, one or more dihydroxy hydroxides and water.

The calcium chloride is in the form of fines. Preferably, the calcium chloride fines range from about a 400 to about 120 Tyler mesh size and, more preferably, about a 200 mesh size.

The calcium chloride may be partially hydrated. It will be appreciated by those skilled in the art that the degree of hydration of a random sample of calcium chloride will contain calcium chloride having various degrees of hydration. Preferably, the calcium chloride is, on average, a dihydrate.

The modified calcium chloride also contains a small proportion of one or more dihydroxy hydroxides. Preferably, the hydroxide is calcium hydroxide, magnesium hydroxide or a mixture thereof. More preferably, the weight ratio of the calcium hydroxide to the magnesium hydroxide is from about 70:30 to about 90:10. Most preferably, the ratio is about 85:15. Preferably, the amount of hydroxide which is used is a predetermined amount which will result in the production of a dry, free flowing solid having a pH of from about 9.0 to about 9.5. More preferably, 110% of said predetermined amount of hydroxide is used. The amount of hydroxide which is required may be determined, in advance, from the absolute normality of the phosphonocarboxylic acid solution and the hydroxides. About 28% of hydroxide, based upon the weight of the chlorides, may be used. Without being limited by theory, it is believed that there is a surface activated reaction between the phosphonocarboxylic acid and the hydroxides to form an acid-salt complex. This complex is bound to the calcium chloride through the water molecules in the mixture. In particular, about 2 or 3 water molecules may be employed in associating the hydroxide/phosphonocarboxylic acid complex to each calcium chloride molecule. The amount of hydroxide which is required is sufficient to neutralize the phosphonocarboxylic acid. Preferably, a slight excess of hydroxide is present. The excess may be about 3 wt. % hydroxide to acid.

The modified calcium chloride may be made in situ. Alternately, a number of commercially available grades of modified calcium chloride, which contain hydroxides as well as other chlorides, may be utilized. One commercial available product is DOW FLAKE 80 fines. In some cases, it may be necessary to add dihydroxy hydroxides to obtain the desired level of dihydroxy hydroxides in the fines. The fines may contain about 5 wt. % of other chlorides. A suitable mixture is set out below:

Calcium chloride: about 77 wt. %
Water: about 12 wt. %
Magnesium hydroxide: about 1 wt. %
Calcium hydroxide: about 1 wt. %
Other chlorides: about 9 wt. %

To prepare the dry, free flowing mixture, an aqueous solution of phosphonocarboxylic acid is added to the calcium chloride. The concentration of phosphonocarboxylic acid in the aqueous solution is preferably from about 30 to 60 wt. % and, more preferably, from about 40 to about 60, and most preferably about 50 wt. %.

Preferably, the amount of active inhibitor (phosphonics) added by the phosphonocarboxylic acid may be up to about 0.4:1 of inhibitor to calcium chloride. The ratio of modified calcium chloride fines to the aqueous phosphonocarboxylic acid solution may be from about 8:1 to about 12:1 and, more preferably, about 9:1 on a weight for weight basis.

The amount of water in the mixture of phosphonocarboxylic acid and modified calcium chloride must be limited to ensure that a dry, free flowing product is obtained. A weight for weight ratio of up to about 1:3.5 of chloride to water may be used. If too much water is present, then the mixture will agglomerate together. In terms of final free flowing product, the total water content is preferably from about 13 to about 23 wt. % and, more preferably, about 17 wt. %.

The modified calcium chloride is placed in an agitated bed. Any suitable reaction vessel may be used. The phosphonocarboxylic acid is then added to this agitated bed at a rate sufficient to produce a dry, flowing product. The phosphonocarboxylic acid is added sufficiently slowly such that no significant lumps are produced. The rate of addition may be in the order of about 20 wt. % acid per hour (about 17.3 grams of a 50 wt. % solution of phosphonocarboxylic acid per quarter of an hour to the modified calcium chloride). The faster the mixing rate, the greater the maximum possible speed of addition may be. The mixing rate may be 1:17 molar ratio of acid to chloride per 15 minutes. The phosphonocarboxylic acid and the modified calcium chloride are mixed until a dry, free flowing product is obtained.

The addition of the phosphonocarboxylic acid to the modified calcium chloride produces an acid salt complex. This dry, free flowing product may be subsequently diluted by mixing the product with, for example, calcium chloride. In such a case, the product may be mixed so that, when dissolved, a substantially neutral pH solution is obtained. Preferably, the pH is in the range from about 7.7 to about 8.1. If calcium chloride is used to dilute the mixture, then the product and the calcium chloride may be mixed in a ratio of about 199:1. Accordingly, one quarter pound of the product may be mixed with about 49.75 pounds of calcium chloride to obtain, when dissolved, a substantially neutral solution.

Accordingly, the dry, free flowing mixture comprises one or more phosphonocarboxylic acids, calcium chloride fines which, on average, are a dihydrate, and a sufficient amount of hydroxide to form a phosphonocarboxylic acid salt mixture having a slightly alkaline pH. Preferably, about 2 wt. % of hydroxide, based upon the weight of the chlorides, is used.

The resultant liquid and dry formulations are inherently safe chemicals. This greatly facilitates the use, handling as well as the application of the formulations.

The following non-limiting examples are illustrative of the present invention.

EXAMPLE 1

Five salt solutions were prepared according to the following method. The amounts of starting materials used in each of the runs, together with the pH measurements of each run, are set out in table 1 below. In each of these runs, the potassium hydroxide was added to a reaction vessel. The magnesium hydroxide was then added to the reaction vessel and the hydroxides were mixed together in the reaction vessel. BELCOR 575 TM (an hydroxyphosphonocarboxylic acid-50% active) was added at a rate sufficient to maintain the temperature of the mixture below 140° F. The mixture was continuously mixed during the addition of the BELCOR 575 TM. The total time taken for the addition of the BELCOR 575 TM to the mixture of hydroxide was 2 hrs., 15 min.

After the solution of BELCOR 575 TM and the hydroxides was prepared, the weight and the specific gravity of the solution were measured. Water was added to adjust the specific gravity as desired. The pH of the mixture was then measured. If the pH of the mixture was too low, then the pH was adjusted upwardly (more basic) by the addition of potassium hydroxide. Conversely, if the mixture was too alkaline, then the pH was reduced by the addition of BELCOR 575 TM. The pH of the mixture after the adjustment was then measured.

TABLE 1

| composition of the neutral salt solutions | | | | | |
|---|---|---|---|---|---|
| MEASUREMENT | Run #1 | Run #2 | Run #3 | Run #4 | Run #5 |
| Magnesium Hydroxide(g) | 1 | 1 | 1 | 1 | 1 |
| Potassium Hydroxide(g) | 50 | 48 | 52 | 51 | 51 |
| BELCOR 575 TM (g) | 50 | 50 | 48 | 49 | 49 |
| Water (g) | 1.5 | 2 | 2 | 1 | 0 |
| pH | 9.91 | 6.87 | 10.1 | 9.35 | 9.36 |
| Adjustment with BELCOR 575 TM (g) | 1 | 0 | 2 | 0 | 0 |
| Adjustment With Potassium Hydroxide (g) | 0 | 1.2 | 0 | 0 | 0 |
| Final pH | 9.25 | 9.6 | 9.37 | 9.35 | 9.36 |

Each of these five runs produced a concentrated solution having a pH of about 9.5. The solution prepared in run numbers 1 and 3 initially had a pH which was too alkaline after the reaction had proceeded to completion and, accordingly had to be adjusted. Similarly, the solution prepared in run #2, after the reaction had proceeded to completion, had a pH which was too acidic and had to be adjusted.

EXAMPLE 2

A substantially neutral salt solution was prepared using the method of Example 1. Table 2 sets out the amount of potassium hydroxide, magnesium hydroxide and BELCOR 575 TM which were used to produce the neutral salt solution as well as the amount of BELCOR 575 TM which was used to adjust the pH of the salt solution.

| MEASUREMENT | |
|---|---|
| Magnesium Hydroxide (lbs) | 9 |
| 3Potassium Hydroxide (lbs) | 450 |
| BELCOR 575 TM (lbs) | 450 |
| pH | 9.82 |
| Adjustment with BELCOR 575 TM (lbs) | 8 |
| Final pH | 9.5 |

COMPARATIVE EXAMPLE 1

A salt solution was prepared from 6 pounds of magnesium hydroxide, 480 pounds of potassium hydroxide and 470 pounds of BELCOR 575 TM. The same method as set out in Example 1 was followed with the exception that the temperature of the solution, during the addition of the BELCOR 575 TM, was allowed to increase at will. The BELCOR 575 TM was added over a period of 45 minutes. The highest temperature achieved during this addition was 198° F. The final pH was 10.0. The specific gravity of the solution was adjusted by the addition of 41.6 pounds of water. The pH was subsequently adjusted by the addition of 7.2 pounds of BELCOR 575 TM. The increased temperature during the production of the solution resulted in the volatization of water and potassium hydroxide. In addition, the increased temperature resulted in a deactivation of some of the phosphonocarboxylic acid.

The same steps were repeated with the exception that the target maximum temperature during the addition of the BELCOR 575 TM was 140° F. The actual maximum temperature which was achieved was 144° F. No water was added to adjust the specific gravity of the resultant solution. The solution had a pH of 9.75 and was adjusted to 9.45 by the addition of 5.0 pounds of BELCOR 575 TM.

When the temperature is controlled by the rate of addition of the BELCOR 575 TM, a consistent neutral salt solution may be obtained without any substantial deactivation of the phosphonocarboxylic acid.

EXAMPLE 3

This experiment demonstrates the production of a dry, free flowing phosphonocarboxylic acid mixture from one kilogram of modified calcium chloride fines and 155.7 grams of BELCOR 575 TM (an hydroxyphosphonocarboxylic acid). The BELCOR 575 TM was added at the varying rates set out below to the fines. The rate of addition is expressed as a weight per cent based on the weight of the fines before the addition of the BELCOR 575 TM. The result was "best" if the product contained more than 99% active phosphonics. The result was "acceptable" if the resultant mixture had active phosphonics. A result was "marginal" if less than 99% of the phosphonics were active. The result was a failure if less than 95% of the phosphonics were active. Batch 1 used 25 lbs. fines, batch 2 used 30 lbs. of fines and batch 3 used 65 lbs. fines.

| BATCH # | RUN # | RATE OF ADDITION | TOTAL ADDITION TIME | RESULT |
|---|---|---|---|---|
| 1 | 1 | 1%/min. | 100 minutes | acceptable |
| 1 | 2 | 5%/min. | 20 minutes | failure |
| 1 | 3 | 50%/hr. | 120 minutes | acceptable |
| 1 | 4 | 75%/hr. | 80 minutes | marginal |
| 2 | 2 | 2%/hr. | 50 hours | acceptable |
| 2 | 2 | 3%/hr. | 33 hours | acceptable |
| 2 | 3 | 4%/hr. | 25 hours | failure |
| 3 | 1 | 1.5%/hr. | 66 hours | good |
| 3 | 2 | 1.75%/hr. | 57 hours | best |
| 3 | 3 | 2.5%/hr. | 40 hours | acceptable |

EXAMPLE 4

A dry, free flowing salt mixture was prepared from 50 pounds of calcium chloride fines and 7.2 lbs. of BELCOR 575 TM. The BELCOR 575 TM was added to the calcium chloride fines, while the fines were being agitated, at a rate of 1.75 weight per cent per minute based on the weight of the fines before the addition of the BELCOR 575. The resultant product was a failure.

The experiment was repeated except the BELCOR 575 TM was added at a rate of 1 weight per cent per minute based on the weight of the fines before the addition of the BELCOR 575. The total addition time was 100 minutes. The resultant product was acceptable.

EXAMPLE 5

A series of concentrated salt solutions were prepared according to the following method. In each of these runs, potassium hydroxide was added to a reaction vessel. Subsequently, BELCOR 575 TM was added at a rate sufficient to maintain the temperature of the mixture below 140° F. The mixture was continuously mixed during the addition of the BELCOR 575 TM. Immediately after the completion of the addition of the potassium hydroxide to the BELCOR 575 TM, the pH of the mixture was measured. The results are set out in the following table.

| RUN # | VOLUME (gallons) | BELCOR 575 TM (lbs.) | POTASSIUM HYDROXIDE(lbs.) | INITIAL pH | FINAL pH |
|---|---|---|---|---|---|
| 1 | 90 | 525 | 525 | 6.5 | 7.85 |
| 2 | 90 | 530 | 530 | 6.2 | 8.00 |
| 3 | 45 | 265 | 265 | 7.0 | 8.01 |
| 4 | 90 | 525 | 525 | 6.5 | 8.05 |
| 5 | 45 | 265 | 265 | 6.6 | 8.75 |
| 6 | 90 | 540 | 540 | 6.8 | 8.65 |
| 7 | 90 | 520 | 520 | 6.9 | 8.80 |
| 8 | 90 | 520 | 520 | 6.8 | 8.65 |
| 9 | 45 | 260 | 260 | 6.8 | 8.41 |
| 10 | 90 | 520 | 520 | 6.5 | 8.61 |

I claim:

1. A process for preparing a substantially active salt solution of one or more phosphonocarboxylic acids comprising preparing a first aqueous solution of one or more phosphonocarboxylic acids, preparing a second aqueous solution of one or more hydroxides and mixing a sufficient amount of said first solution into said second solution to obtain a mixture of said first and second solutions having a slightly alkaline pH, said first solution being introduced into said second solution at a rate to maintain the pH of said second solution at the point of addition of said first solution less than about 12 during said addition.

2. The process as claimed in claim 1 wherein said second solution comprises a major proportion of potassium hydroxide.

3. The process as claimed in claim 2 wherein said second solution also comprises a pH stabilizing amount of magnesium hydroxide.

4. The process as claimed in claim 3 wherein said mixture comprises at least about 2 wt. %, based on the weight of the final mixture, of potassium hydroxide.

5. The process as claimed in claim 2 wherein, during the introduction of said second solution into said first solution, the temperature of said mixture is maintained below about 150° F.

6. The process as claimed in claim 5 wherein the temperature is maintained below about 140° F.

7. The process as claimed in claim 2 wherein said mixture has a concentration of from about 150,000 to about 450,000 ppm of phosphonocarboxylic acid and the pH of said mixture immediately after said mixing step is substantially neutral.

8. The process as claimed in claim 7 wherein the said substantially neutral pH is from about 6.5 to about 8.5.

9. The process as claimed in claim 7 wherein said one or more phosphonocarboxylic acids reacts said one or more hydroxides and said mixture is allowed to stand until said reaction proceeds to completion.

10. The process as claimed in claim 9 wherein said pH of said mixture after said reaction has proceeded to completion is about 9.5 and said mixture is then diluted to obtain a solution having a pH from about 8.0 to about 8.5.

11. The process as claimed in claim 1 wherein said slightly alkaline pH is about 8.0 to about 8.5.

12. The process as claimed in claim 11 wherein said one or more phosphonocarboxylic acids are hydroxyphosphonocarboxylic acids.

13. The process as claimed in claim 11 wherein the concentration of said one or more phosphonocarboxylic acids in said first solution is from about 30 to about 60 wt. %.

14. The process as claimed in claim 1 wherein said second solution of one or more hydroxides comprises an aqueous solution of potassium hydroxide and an aqueous solution of magnesium hydroxide, said potassium hydroxide being mixed with said first solution of phosphonocarboxylic acids to prepare said salt solution and, during said mixing said solution of magnesium hydroxide is used in place of said potassium hydroxide solution as the temperature of said salt solution approaches 140° F.

15. A substantially neutral and substantially active salt solution of one or more phosphonocarboxylic acids when prepared by the process of claims 1, 2 or 10.

16. A process for the production of a dry, free flowing phosphonocarboxylic acid-containing product comprising the steps of preparing a dry mixture of a major proportion of partially hydrated calcium chloride fines and a minor amount of one or more dihydroxy hydroxides, preparing an aqueous solution of one or more phosphonocarboxylic acids and adding a sufficient amount of said solution to said dry mixture, with agitation, at a rate to obtain said dry, free flowing product and to maintain the pH of said dry mixture at the point of addition of said aqueous solution less than about 12 during said addition.

17. The process as claimed in claim 16 wherein said calcium chloride is a dihydrate.

18. The process as claimed in claim 16 wherein said compound has a moisture content from about 13 to about 23 percent by weight.

19. The process as claimed in claim 18 wherein the Tyler mesh size of said fines ranges from about 400 to about 120.

20. The process as claimed in claim 16 wherein there is a slight excess of said hydroxide in said product as compared to said acid.

21. The process as claimed in claim 20 wherein the excess is about 3%.

22. The process as claimed in claim 16 wherein the ratio of modified calcium chloride fines to the aqueous phosphonocarboxylic acid solution is from about 8:1 to about 12:1 on a weight for weight basis.

23. The process as claimed in claim 16 wherein said one or more hydroxides comprises magnesium hydroxide, calcium hydroxide or a mixture thereof.

24. The process as claimed in claim 23 wherein said mixture contains a predetermined amount of hydroxide such that said product has a pH of from about 9.0 to about 9.5.

25. The process as claimed in claim 24 wherein said mixture contains about 110% of said predetermined amount of magnesium hydroxide.

26. A dry, free flowing phosphonocarboxylic acid mixture when prepared by the process of claims 16, 23 or 25.

* * * * *